US005610311A

United States Patent [19]
Marble et al.

[11] Patent Number: 5,610,311
[45] Date of Patent: Mar. 11, 1997

[54] REACTION OF METAL SALT OF AN S-SUBSTITUTED N-CYANODITHIOMINOCARBONATE WITH HYDRAZINE OR HYDRAZINE HYDRATE

[75] Inventors: Lyndon K. Marble, Germantown; Wallace E. Puckett, Bartlett, both of Tenn.

[73] Assignee: Buckman Laboratories International, Inc., Memphis, Tenn.

[21] Appl. No.: 425,221

[22] Filed: Apr. 18, 1995

Related U.S. Application Data

[63] Continuation of Ser. No. 62,532, May 18, 1993, abandoned.
[51] Int. Cl.$^6$ .................................................. C07D 249/08
[52] U.S. Cl. ........................................................ 548/255
[58] Field of Search ............................................. 548/255

[56] References Cited

U.S. PATENT DOCUMENTS

| | | |
|---|---|---|
| 2,816,136 | 12/1957 | Pera . |
| 2,881,070 | 4/1959 | Pera . |
| 2,881,071 | 4/1959 | Buckman et al. . |
| 3,299,129 | 1/1967 | D'Amico . |
| 4,543,309 | 9/1985 | Hirabayashi et al. . |
| 5,068,347 | 11/1991 | Puckett et al. . |

FOREIGN PATENT DOCUMENTS

| | | |
|---|---|---|
| 221221 | 1/1986 | Czechoslovakia . |
| 0142152 | 5/1985 | European Pat. Off. . |
| 256693A1 | 5/1988 | Germany . |
| 181743 | 4/1985 | Hungary . |
| 1232838 | 5/1971 | United Kingdom . |

OTHER PUBLICATIONS

Hantzsch and Wolvekamp, Liebigs Ann. Chem. 331:265–97 (1904.

Wittenbrook, "The Chemistry of N–Cyanodithioimidocarbonic Acid. III. An Intermediate in Heterocyclic Synthesis," J. Heterocyclic Chem. 12:37–42 (1975).

Timmons and Wittenbrook, "The Chemistry of Cyanodithioimidocarbonic Acid," J. Org. Chem. 32:1566–72 (1967).

Suyama and Odo, "Synthetic Study of Cyanamidedithiocarbonic Acid Ester and Related Compounds (Part 1), " J. Syn. Org. Chem. (Japan) 29:65–73 (1971) (includes English language abstract).

Walek, Preiss, and Dietzel, Z. Chem. 18(4):144–45 (1978).

Trompen, Geevers and Hackmann, "Addition of Chlorine to the Cyanogen Bond IV," Rec. Trav. Chim. 90:463–68 (1971).

Wieland, Ph.D. dissertation, "A Nuclear Magnetic Resonance Study Part I. Conformational Inversion in 9,10–Dihydro–9,10–o–Xylyleneanthracene; Part II. Chemical Rate Processes of N–Cyanoimines," West Virginia University (1971).

D'Amico and Campbell, "Derivatives of Potassium Cyanodithioimidocarbonate. I. Synthesis of 1,4,6,9–Tetrathiaspiro[4.4]nonane and Related Compounds," J. Org. Chem. 32:2567–70 (1967).

Thaler and McDivitt, "The Synthesis and Some Reactions of 1,2,4–Thiadiazolylsulfenyl Chlorides," J. Org. Chem. 36(1):14–18 (1971).

Wittenbrook, Smith and Timmons, "The Chemistry of N–Cyanodithioimidocarbonic Acid. II. Synthesis of 3–Halo–1,2,4–thiadiazoles," J. Org. Chem. 38(3):465–71 (1973).

Wobig, "Reaktioen von Cyanimidodithiocarbonaten und Cyanthioharnstoffsalzen mit γ–Bromocrotonsaure–derivaten," Liebigs Ann. Chem. (1978) pp. 1118–1122.

Leysen, Haemers and Bollaert, "Thiazolopyridine Analogs of Nalidixic Acid. 2. Thiazolo[4,5–b]pyridines," J. Heterocyclic Chem. 21:1361–66 (1984).

Krapivin, Jurasek, Kovac and Kul'nevich, "Synthesis and Properties of 4–Amino–5–(5–X–2–Furyl)Thiazole Derivatives," Collection Czechoslovak Chem. Commun. 49:2285–94 (1984).

Gattow and Klaeser, Z. Anorg. Allg. Chem. 433:211–16 (1977).

Godfrey and Kurzer, "Heterocyclic Compounds from Urea Derivatives. Part I. A New Synthesis of 3–Amino–5–mercapto(and –hydroxy)–1,2,4–triazoles," J. Chem. Soc. (1960) pp. 3437–3444.

*Primary Examiner*—Joseph Conrad
*Attorney, Agent, or Firm*—Finnegan, Henderson, Farabow, Garrett & Dunner, L.L.P.

[57] ABSTRACT

Processes for the preparation of a metal salt of 3-mercapto-5-amino-(1H)-1,2,4-triazole or 3-mercapto-5-amino-(1H)-1,2,4-triazole, and a novel compound, sodium methyl N-cyanodithioiminocarbonate.

36 Claims, No Drawings

REACTION OF METAL SALT OF AN S-SUBSTITUTED N-CYANODITHIOIMINOCARBONATE WITH HYDRAZINE OR HYDRAZINE HYDRATE

This application is a continuation, of application Ser. No. 08/062,532 filed May 18, 1993, now abandoned.

The invention relates to processes for the preparation of 3-mercapto-5-amino-(1H)-1,2,4-triazole or a salt of 3-mercapto-5-amino-(1H)-1,2,4-triazole.

Broadly, the process of the invention involves the step of contacting a metal salt of the anion of formula I,

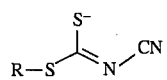
I wherein R—S is any suitable leaving group, with hydrazine or hydrazine hydrate for a sufficient time to form a metal salt of 3-mercapto-5-amino- (1H) -1,2,4 -triazole. The metal salt of 3-mercapto-5-amino- (1H) -1,2,4-triazole may be converted to 3-mercapto-5-amino- (1H) -1,2,4-triazole.

The invention also relates to a novel compound sodium methyl N-cyanodithioiminocarbonate.

3-mercapto-5-amino- (1H) -1,2,4-triazole has utility as an intermediate in organic synthesis. For example, European Patent Application No. 142,152, describes the preparation of organic herbicidal compounds from 3-mercapto-5-amino-(1H) -1,2,4-triazole.

U.S. Pat. No. 5,068,347, describes the rearrangement of 2,5-diamino-1,3,4-thiadiazole at 80° C. in aqueous NaOH. British Patent No. 1,232,838 describes the condensation of carbon disulfide and a salt of aminoguanidine to produce guanidinodithiocarbarmic acid which was then treated with boiling alkali to produce a triazole. U.S. Pat. No. 4,543,309 describes the cyclization of N-guanidinothiourea hydrochloride in refluxing aqueous caustic followed by acidification. Godfrey and Kurzer, *J. Chem. Soc.* (1960) 3437, treated [amino(amidino)]thioureas with acid which produced a triazole and amine and ketone by-products.

For the purposes of the invention, the term "metal salts" includes metal salts having monovalent, bivalent and fractions of polyvalent metals sufficient to balance the anionic charge in the salt. Mixed metal salts are also contemplated. Also, the term "metal hydroxide" includes hydroxides of monovalent, bivalent and polyvalent metals.

For the purposes of the invention, the term "Group 1 or Group 2 metals" includes all metals from Groups 1 and 2 of the Periodic Table.

Also, for the purposes of the invention, the term "methanolic solvent system" includes methanol, aqueous methanol, or any mixture of solvents including methanol. For example, a methanolic solvent system may include methanol and one or more other solvents, such as water, ethanol or acetone.

The invention provides a novel process for preparing 3-mercapto-5-amino-(1H)-1,2,4-triazole or a salt of 3-mercapto-5-amino-(1H)-1,2,4-triazole. The invention can also provide a process for preparing 3-mercapto-5-amino-(1H)-1,2,4-triazole or a salt of 3-mercapto-5-amino-(1H)-1,2,4-triazole which can be rapid and efficient and which can provide good product yield and purity.

One aspect of the invention is to provide a process involving the step of contacting a Group 1 or 2 metal salt of the anion of formula I,

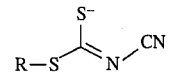
I wherein R—S is any suitable leaving group, with hydrazine or hydrazine hydrate for a sufficient time to form a Group 1 or 2 metal salt of 3-mercapto-5-amino-(1H)-1,2,4-triazole. The Group 1 or 2 metal salt of 3-mercapto-5-amino-(1H)-1,2,4-triazole may be converted to 3-mercapto-5-amino-(1H)-1,2,4-triazole.

Another aspect of the invention is the preparation of a Group 1 or 2 metal salt of the anion of formula I by a process involving the steps of:

(a) contacting cyanamide, carbon disulfide, and a Group 1 or 2 metal hydroxide, in a methanolic solvent system, under conditions sufficient to produce a Group 1 or 2 metal salt of the anion of formula II

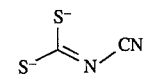
II (b) contacting said Group 1 or 2 metal salt of the anion of formula II of (a) with a compound containing an R-group under conditions sufficient to form a Group 1 or 2 metal salt of the anion of formula I

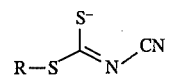
I wherein said R—S group is any suitable leaving group.

An aspect of the invention is also to provide a novel compound sodium methyl N-cyanodithioiminocarbonate.

Other features and advantages of the invention will be set forth in the description which follows, and in part will be apparent from the description, or may be learned by practice of the invention. The features and advantages of the invention may be realized and obtained by means of the processes set out in the appended claims.

The invention is directed to a process for the preparation of a salt of 3-mercapto-5-amino-(1H)-1,2,4-triazole which involves the step of contacting a Group 1 or 2 metal salt of the anion of formula I,

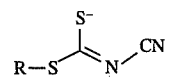
I wherein R—S is any suitable leaving group, with hydrazine or hydrazine hydrate for a sufficient time to form a Group 1 or 2 metal salt of 3-mercapto-5-amino-(1H)-1,2,4-triazole. The salt of 3-mercapto-5-amino-(1H)-1,2,4-triazole may be converted to 3-mercapto-5-amino-(1H)-1,2,4-triazole, preferably by acidification.

In a preferred embodiment, this process uses a Group 1 metal (A) and may be depicted as follows:

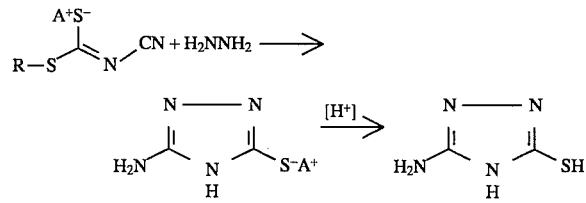

The Group 1 or 2 metal salt of the anion of formula I may be prepared by a process which involves the steps of:

(a) contacting cyanamide, carbon disulfide, and a Group 1 or metal hydroxide, in a methanolic solvent system, under conditions sufficient to produce a Group 1 or 2 metal salt of the anion of formula II

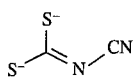
II (b) contacting said Group 1 or 2 metal salt of the anion of formula II of (a) with a compound containing an R-group under conditions sufficient to form a Group 1 or 2 metal salt of the anion of formula I

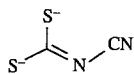
I wherein said R—S group is any suitable leaving group.

In a preferred embodiment, this process uses a Group 1 metal (A) and a compound containing an R-group (R-X). This process may be depicted as follows:

$CS_2 + H_2NCN + 2 A-OH \longrightarrow$

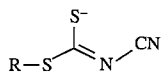

A combination of the above two processes involves the steps of:

(a) contacting cyanamide, carbon disulfide, and a Group 1 or 2 metal hydroxide under conditions sufficient to produce a Group 1 or 2 metal salt of the anion of formula II

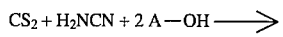
II (b) contacting said Group 1 or 2 metal salt of the anion of formula II of (a) with a compound containing an R-group under conditions sufficient to form a Group 1 or 2 metal salt of the anion of formula I

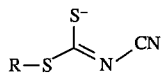
I wherein said R—S group is any suitable leaving group; and (c) contacting the Group 1 or 2 metal salt of the anion of formula I with hydrazine or hydrazine hydrate under sufficient conditions to produce a Group 1 or 2 metal salt of 3-mercapto-5-amino-(1H)-1,2,4-triazole. This process may further involve a step (d) of converting the Group 1 or 2 metal salt of 3-mercapto-5-amino-(1H)-1,2,4-triazole to 3-mercapto-5-amino-(1H)-1,2,4triazole, preferably by acidification.

In a preferred embodiment, this process uses a Group 1 metal (A) and a compound containing an R-group (R-X). This process may be depicted as follows:

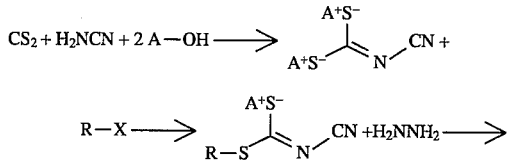

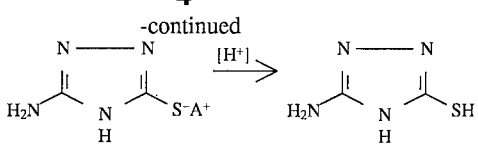

In a further preferred embodiment, a Group 1 or 2 metal salt of 3-mercapto-5-(1H)-1,2,4-triazole can be prepared in high yield and high purity by preparing a metal salt of N-cyanodithioiminocarbonate, which is then used to prepare a metal salt of S-substituted N-cyanodithioiminocarbonate, which is then reacted with hydrazine or hydrazine hydrate to produce a Group 1 or 2 metal salt of 3-mercapto-5-amino-(1H)-1,2,4-triazole. The metal salt of 3-mercapto-5-amino-(1H)-1,2,4-triazole may then be converted to 3-mercapto-5-amino-(1H)-1,2,4-triazole by means known to those skilled in the art, such as acidification.

The above reactions of the invention and their preferred reactants and conditions are detailed below.

Preparation of Metal Salts of N-Cyanodithioiminocarbonates

Metal salts of N-cyanodithioiminocarbonates have been prepared by various methods, such as contacting cyanamide and carbon disulfide, in a solvent of aqueous ethanol, water or absolute ethanol, with a solution of a metal hydroxide. For example, Timmons and Wittenbrook, *J. Org. Chem.*, 32, 1566 (1967) refer to a preparation of a metal salt of N-cyanodithioiminocarbonate in which solid cyanamide and solid potassium hydroxide react in ethanol followed by isolation of the precipitated solid product.

Wieland, Ph.D. dissertation, West Virginia University (1971), and D'Amico and Campbell, *J. Org. Chem.*, 32, 2567 (1967) describe a process involving the reaction of aqueous cyanamide and aqueous KOH in 85-90% ethanol followed by isolation of the precipitated solid. Hungarian Patent No. 181,743 (Reiter) describes the reaction of aqueous cyanamide and aqueous KOH in 60% ethanol followed by isolation of the dipotassium salt product. U.S. Pat. No. 2,816,136 (Pera) refers to the reaction of alkali or alkaline earth metal hydroxides and alkali or alkaline earth metal cyanamides in an all-aqueous system.

The preparation of a Group 1 or 2 metal salt of N-cyanodithioiminocarbonate may involve contacting cyanamide, carbon disulfide, and a Group 1 or 2 metal hydroxide, under conditions sufficient to produce a Group 1 or 2 metal salt of the anion of formula II

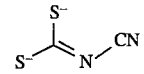
II

Preferably, the preparation of a Group 1 or 2 metal salt of N-cyanodithioiminocarbonate involves contacting cyanamide, carbon disulfide, and Group 1 or 2 metal hydroxide in any suitable solvent. More preferably the solvent is methanol, aqueous methanol, water, ethanol, aqueous ethanol, acetone or mixtures of these. Most preferably, the cyanamide, carbon disulfide, and Group 1 or 2 metal are contacted in a methanolic solvent system.

In a preferred embodiment according to the invention, a solution of aqueous cyanamide and carbon disulfide is contacted with a Group 1 (alkaline) metal hydroxide, in a methanolic solvent system, to produce a bis-alkaline metal salt of N-cyanodithioiminocarbonate.

The preferred methanolic solvent system may be methanol, aqueous methanol, or any mixture of solvents including methanol. For example, a methanolic solvent system may include methanol and one or more other solvents, such as water, ethanol or acetone. Preferably, the amount of methanol in the reaction mixture is at least 25% of the total volume, excluding the carbon disulfide volume. More preferably, the amount of methanol in the reaction mixture is about 90% of the total volume, excluding the carbon disulfide volume. Most preferably, the amount of methanol in the reaction mixture is about 50% of the total volume, excluding the carbon disulfide volume. Lower percentages of methanol may also be used. The reaction mixture containing a lower percentage of methanol may have some green or orange discoloration, which is not necessarily undesirable.

In a further preferred embodiment of the invention, a mixture of aqueous cyanamide, preferably in a 50% aqueous solution, and carbon disulfide ($CS_2$) in methanol, preferably 50% by volume of the total solution volume, excluding the $CS_2$ volume, is cooled preferably to 20° C. and a metal hydroxide, preferably a 50% aqueous solution, is added preferably over a 45 minute period. The reaction can be completed in about 2 hours. This reaction produces a yellow solution with a neutral to alkaline pH of generally 7–8.5.

The preferred use of a methanolic solvent system in the production of metal salts of N-cyanodithioiminocarbonate can be a significant improvement over other solvent systems. For example, the reaction for the production of a bis-alkaline metal salt of N-cyanodithioiminocarbonate may be performed in ethanol. However, a reaction in a methanolic solvent system possesses several advantages over a reaction in ethanol or other known solvents including, inter alia, a lower cost, a greater ease of separation from water for reuse, and a higher purity product.

These metal salts of N-cyanodithioiminocarbonates can be used in further reactions, for example, to produce a mono-alkaline metal salt of mono-S-substituted N-cyanodithioiminocarbonate. The metal salts of N-cyanodithioiminocarbonates may be kept in the methanolic solvent system or they may be isolated prior to further reactions.

Preparation of Metal Salts of Mono-S-Substituted N-Cyanodithioiminocarbonates

A mono-S-substituted N-cyanodithioiminocarbonate has been prepared by a method reported by Timmons and Wittenbrook, *J. Org. Chem.*, 32:1566 (1967). In Timmons and Wittenbrook, potassium methyl N-cyanodithioiminocarbonate is prepared by adding a solution of methyl iodide in acetone at about 0° C. to an aqueous acetone solution of dipotassium N-cyanodithioiminocarbonate. The reaction mixture is concentrated, and the product is freed from the potassium iodide (KI) by-product by dissolving the product in acetone and removing the KI by filtration. The acetone solution is concentrated and the solid product is washed with ether.

The preparation of a metal salt of mono-S-substituted N-cyanodithioiminocarbonate may involve contacting a Group 1 or 2 metal salt of the anion of formula II

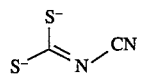

II with at least one compound containing an R-group under conditions sufficient to form a Group 1 or 2 metal salt of the anion of formula I

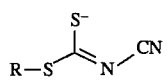

I wherein the R—S group is any suitable leaving group. Preferably, the compound or compounds containing an R-group preferably provide at least one molar equivalent of the group R and less than two molar equivalents of the group R.

Preferably, the preparation of a Group 1 or 2 metal salt of mono-S-substituted N-cyanodithioiminocarbonate involves contacting a Group 1 or 2 metal salt of the anion of formula II and at least one compound containing an R-group in any suitable solvent. More preferably the solvent is methanol, aqueous methanol, water, ethanol, aqueous ethanol, acetone or mixtures of these. Most preferably, the Group 1 or 2 metal salt of the anion of formula II and at least one compound containing an R-group are contacted in a methanolic solvent system.

The preferred preparation of a metal salt of mono-S-substituted N-cyanodithioiminocarbonate in a methanolic solvent system according to the invention can be more rapid and efficient than the prior art processes. Preferably, the methanolic solvent system may be methanol, aqueous methanol, or any mixture of solvents including methanol, as described above. Preferred methanolic solvent systems for the preparation of metal salts of mono-S-substituted N-cyanodithioiminocarbonates are the same as those described for the preparation of metal salts of N-cyanodithioiminocarbonates.

The group represented by R is preferably selected from substituted or unsubstituted, branched or unbranched $C_1$–$C_{20}$ alkyl, $C_2$–$C_{20}$ alkenyl or $C_2$–$C_{20}$ alkynyl groups; monocyclic or polycyclic, fused or nonfused, carbocyclic or heterocyclic, substituted or unsubstituted aryl groups; hydrogen; and non-aryl, monocyclic or polycyclic, fused or nonfused, substituted or unsubstituted heterocyclic groups; or R—S is preferably selected from thiosulfonates; sulfonates, thioesters and thiocarbamates. In a further preferred embodiment, R is selected from substituted or unsubstituted, branched or unbranched $C_1$–$C_6$ alkyl groups. More preferably, R is methyl, ethyl, propyl, or isopropyl, and most preferably, R is methyl.

In a preferred embodiment, the compound containing an R-group is a group R—X, wherein X is chloride, iodide, bromide or a group R—X—R, wherein X is a divalent group such as sulfate ($SO_4^{2-}$). For example, the compound containing an R-group may be selected from methylating agents $CH_3X$ and $(CH_3)_2X$, such as methyl chloride, methyl iodide, or dimethyl sulfate. In a preferred embodiment, the compound containing an R-group is methyl chloride or dimethyl sulfate.

In a preferred embodiment of the invention, an aqueous methanolic solution of a bis-alkaline metal salt of N-cyanodithioiminocarbonate, such as disodium N-cyanodithioiminocarbonate or dipotassium N-cyanodithioiminocarbonate, is treated with a compound containing an R-group, such as methyl chloride, dissolved in methanol or neat, preferably neat, until the reaction to prepare a mono-S-substituted N-cyanodithioiminocarbonate, such as sodium methyl N-cyanodithioiminocarbonate or potassium methyl N-cyanodithioiminocarbonate, is complete, generally about 2 hours. The reaction mixture can be concentrated to recover the methanol and isolate the reaction product.

Where the salt is a sodium salt, the sodium methyl N-cyanodithioiminocarbonate product can be obtained as a viscous yellow mixture which can contain NaCl. Where the salt is a potassium salt, the potassium methyl N-cyanodithioiminocarbonate product can be obtained as a yellow-white solid.

In a preferred embodiment, the mono-S-substituted N-cyanodithioiminocarbonate product can be purified with at least one solvent, such as acetone and/or dichloromethane, prior to further reactions. A purification step may be performed to render the mono-S-substituted N-cyanodithioiminocarbonate product essentially, or totally, free of by-products.

The solid product may be freed from by-products, such as NaCl or KCl, by dissolving the product in a suitable solvent, such as acetone, and filtering. The solvent solution can then be concentrated to recover the solvent and, if concentrated, the resulting solid can be purified by suspending in a suitable solvent, such as dichloromethane, for a suitable time, such as 30 minutes, with agitation. The resultant slurry can then be filtered and the solid can be dried. Any disubstituted ester, such as the dimethyl ester, of N-cyanodithioiminocarbonate which may have formed during the reaction can be isolated from the filtrate.

The preferred use of dichloromethane for the purification is an improvement over the use of diethyl ether because, unlike diethyl ether, dichloromethane is not flammable and does not form peroxides. The product may then be dried either in air for about twelve hours or under vacuum at about 50° C. for about two hours.

These metal salts of S-substituted N-cyanodithioiminocarbonate, which are preferably essentially free of contaminants, may be further reacted with hydrazine or hydrazine hydrate to produce a metal salt of 3-mercapto-5-amino-(1H)-1,2,4-triazole.

Preparation of Metal Salts of 3-Mercapto-5-amino-(1H)-1,2,4-Triazole

The reaction of a metal salt of mono-S-substituted N-cyanodithioiminocarbonate with hydrazine or hydrazine hydrate was unknown prior to the invention and is disclosed here as a novel reaction.

A preferred embodiment of the invention is a process comprising the step of contacting a Group 1 or 2 metal salt of the anion of formula I,

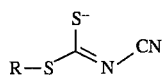

wherein R—S is any suitable leaving group, with hydrazine or hydrazine hydrate for a sufficient time to form a Group 1 or 2 metal salt of 3-mercapto-5-amino-(1H)-1,2,4-triazole.

A further preferred embodiment of the invention is a process comprising the steps of:

(a) contacting cyanamide, carbon disulfide, and a Group 1 or 2 metal hydroxide under conditions sufficient to produce a Group 1 or 2 metal salt of the anion of formula II

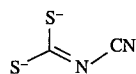

(b) contacting said Group 1 or 2 metal salt of the anion of formula II of (a) with a compound containing an R-group under conditions sufficient to form a Group 1 or 2 metal salt of the anion of formula I

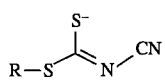

wherein said R—S group is any suitable leaving group; and (c) contacting the Group 1 or 2 metal salt of the anion of formula I with hydrazine or hydrazine hydrate under sufficient conditions to produce a Group 1 or 2 metal salt of 3-mercapto-5-amino-(1H)-1,2,4-triazole.

In each of the processes for the preparation of metal salts of 3-mercapto-5-amino-(1H)-1,2,4-triazole, the group R, and the preferred embodiments of the group R, are the same as those described previously for the preparation of metal salts of mono-S-substituted N-cyanodithioiminocarbonates. As described above, in a particularly preferred embodiment, R is methyl, ethyl, propyl, or isopropyl, and most preferably, R is methyl.

The reaction to form a metal salt of 3-mercapto-5-amino-(1H)-1,2,4-triazole generally can be conducted at elevated temperatures in the range of 25° C. to 100° C., although the reaction is not limited to this range. In a preferred embodiment, the reaction temperature is in the range of about 50° C. to 60° C.

In a preferred embodiment, a salt of mono-S-substituted N-cyanodithioiminocarbonate, such as potassium methyl N-cyanodithioiminocarbonate or sodium methyl N-cyanodithioiminocarbonate, can be dissolved in water at room temperature and a molar equivalent of hydrazine or hydrazine hydrate can be added dropwise, portion wise or all at once, with agitation or stirring. Molarities of the salt are preferably in the range of 0.5M to 4M, and molarities in the range of 2M to 4M are more preferred. The reaction is exothermic and the reaction temperature is preferably maintained at about 50° C. by controlling the rate of addition until all of the hydrazine or hydrazine hydrate is added. After addition of the hydrazine or hydrazine hydrate, the reaction mixture is preferably kept at about 50° C. for preferably 1.5 hours or until completion of the reaction, after which the mixture is cooled.

A metal salt of 3-mercapto-5-amino-(1H)-1,2,4-triazole may be used to produce 3-mercapto-5-amino-(1H)-1,2,4-triazole.

Preparation of 3-mercapto-5-amino-(1H)-1,2,4.triazole

A metal salt of 3-mercapto-5-amino-(1H)-1,2,4-triazole may be converted to 3-mercapto-5-amino-(1H)-1,2,4-triazole by any means known to those skilled in the art.

In a preferred embodiment, a metal salt of 3-mercapto-5-amino-(1H)-1,2,4-triazole may be converted to 3-mercapto-5-amino-(1H)-1,2,4-triazole by acidification. Preferably, the acidification is performed by adding a sufficient amount of acid to the solution of a metal salt of 3-mercapto-5-amino-(1H)-1,2,4-triazole until the solution reaches a pH of about 4 to less than about 7. More preferably, a sufficient amount of an acid, such as hydrochloric acid, is added to the solution of a metal salt of 3-mercapto-5-amino-(1H)-1,2,4-triazole until the solution reaches a pH of about 6.

In a preferred embodiment, the solid 3-mercapto-5-amino-(1H)-1,2,4-triazole product can be washed with water or acetone, isolated by filtration, and dried. The yield of the 3-mercapto-5-amino-(1H)-1,2,4-triazole is preferably in the range of 75 to 100% and the product purity is preferably in excess of 94%.

The following examples are illustrative of the invention and are not intended to limit the scope of the invention.

Disodium N-Cyanodithioiminocarbonate

EXAMPLE 1

Cyanamide (40.5 g of 50% aqueous solution, 482 mmol, 1.0 equiv), 95% ethanol (96 mL), and carbon disulfide (36.6 g, 481 mmol, 1.0 equiv) were charged into a 1-L, three-necked, round-bottomed flask fitted with a thermometer, mechanical stirring paddle, addition funnel and nitrogen valve. The vessel was then purged with nitrogen for 10 minutes. The mixture was agitated and cooled to 5° C. A solution of base was prepared separately. Sodium hydroxide (38.6 g, 965 mmol, 2.0 equiv) was dissolved in 550 mL 95% ethanol over ½ h and the solution was cooled to room temperature. The addition funnel was charged with this solution. The solution of base was added to the cooled cyanamide mixture over 25 minutes while maintaining a temperature of 9° C. The yellow product mixture was stirred for 1 hour, and then the insoluble material was removed by filtration. This solution of disodium N-cyanodithioiminocarbonate was used directly in a further reaction to produce sodium methyl N-cyanodithioiminocarbonate.

EXAMPLE 2

Cyanamide (10.2 g of a 50% aqueous solution; 120.5 mmol, 1.0 equiv), 95% ethanol (60 mL), and carbon disulfide (9.24 g, 121.4 mmol, 1.01 equiv) were charged into a 100-mL, three-necked, round-bottomed flask fitted with a thermometer, nitrogen valve, an addition funnel (non-equalizing) and a stirring bar. The addition funnel was charged with sodium hydroxide (9.64 g, 241 mmol, 2.0 equiv) dissolved in 17 mL water. The cyanamide mixture was cooled to 1° C. and the base solution was added dropwise over 34 minutes. The final temperature was 10° C. and the temperature was allowed to rise to 15° C. over 1 hour. The mixture was concentrated in vacuo, and the residual water was chased with 95% ethanol (2×50 mL). The yellow-white solid was suspended in ethanol, stirred for 10 minutes and filtered to yield 5.4 g (27%) of the disodium N-cyanodithioiminocarbonate as a white powder. The filtrate was concentrated to yield 16 g of slightly wet product.

EXAMPLE 3

In addition to the methods listed in Examples 1 and 2, disodium N-cyanodithioiminocarbonate can be prepared in other solvents such as aqueous ethanol (25 to 60% water, preferably 50% water) or aqueous methanol (5 to 75% water, preferably 50% water) and at temperatures between 0° and 30° C.

Dipotassium N-Cyanodithioiminocarbonate

EXAMPLE 4

Cyanamide (125.6 g of a 50% aqueous solution, 1.496 mol, 1.0 equiv), 95% ethanol (350 mL), and carbon disulfide (123.15 g, 1.617 mol, 108 equiv) were charged into a 1-L stainless steel autoclave. The system was sealed and potassium hydroxide (14.0M, 213.7 mL, 2.992 mol, 2.0 equiv.) was pumped in over 20 minutes while the reaction temperature was maintained at under 30° C. Water (30 mL) and 95% ethanol (30 mL) were used as rinses for the hydroxide. The mixture was stirred for 2 h, and the resulting yellow slurry was used directly in a further reaction to produce potassium methyl N-cyanodithioiminocarbonate.

EXAMPLE 5

Cyanamide (15.16 g of a 50% aqueous solution, 180 mmol, 1.0 eguiv), methanol (40 mL), and carbon disulfide (13.7 g, 180 mmol, 1.0 eguiv) were charged into a 100-mL, three-necked, round-bottomed flask equipped with a stirring bar, thermometer, and addition funnel. The system was sealed and potassium hydroxide (14.0M, 25,7 mL, 360 mmol, 2.0 equiv) was added over 18 minutes while the reaction temperature was maintained at under 20° C. The mixture was stirred for 2 h and the resulting yellow slurry was tested for residual cyanamide, and its pH was determined. Since cyanamide remained (TLC) and the pH was greater than 12, carbon disulfide (3 mL) was added to give the reaction mixture a pH of 9 after 15 minutes. This slurry was used directly in a further reaction to produce potassium methyl N-cyanodithioiminocarbonate.

Sodium Methyl N-Cyanodithioiminocarbonate

EXAMPLE 6

An aqueous solution of disodium N-cyanodithioiminocarbonate (prepared according to U.S. Pat. No. 2,816,136, which is incorporated herein by reference), 32% by weight in water; 100 mL, 197 mmol) was diluted with acetone (160 mL) and water (79 mL). The solution was cooled to 5° C. and a solution of methyl iodide (28.0 g, 197.3 mmol, 1.00 equiv) in acetone (80 mL) was added dropwise over 45 minutes. The mixture was concentrated to a yellow slurry with a mass of 57 g (30 g theoretical yield). This slurry could be used as is in a further reaction to produce either 3-mercapto-5-amino-(1H)-1,2,4-triazole or dimethyl N-cyanodithioiminocarbonate assuming a 95% conversion to the S-methyl adduct. Alternatively, the compound can be isolated and identified by methods well known in the art.

EXAMPLE 7

Example 6 was repeated using a methylating agent of dimethyl sulfate in place of methyl iodide, with the exception that the product sodium methyl N-cyanodithioiminocarbonate (57 g, as a yellow slurry) was converted to dimethyl N-cyanodithioiminocarbonate in a further reaction with a second equivalent of methyl iodide.

EXAMPLE 8

An aqueous solution of disodium N-cyanodithioiminocarbonate (prepared according to U.S. Pat. No. 2,816,136, which is incorporated herein by reference) (32% by weight in water; 250 mL, 493 mmol) was diluted with acetone (250 mL). Dimethyl sulfate (62.2 g, 493 mmol, 1.0 equiv.) was added dropwise over 12 minutes, and the reaction temperature was allowed to rise to 50° C. The mixture was stirred for 1 hour while the temperature gradually decreased to 25° C. After 1 h, the mixture was concentrated to a yellow slurry with a volume of 250 mL. The slurry was diluted with acetone (1 L), filtered to remove sodium methyl sulfate, and concentrated to a volume of 150 mL. This slurry could be used as is in a further reaction to produce either 3-mercapto-5-amino-(1H)-1,2,4-triazole or dimethyl N-cyanodithioiminocarbonate, assuming a 95% conversion to the S-methyl adduct. Alternatively, the compound can be isolated and identified by using methods known in the art.

EXAMPLE 9

Example 8 was repeated using a reaction temperature of 5° C., with the exception that the addition of dimethyl sulfate required 50 minutes. The slurry was used as is in a further reaction to produce dimethyl N-cyanodithioiminocarbonate. The slurry could also be used to produce a high yield of 3-mercapto-5-amino-(1H)-1,2,4-triazole, assuming a 95% conversion to the S-methyl adduct. Alternatively, the compound can be isolated and identified by methods known in the art.

EXAMPLE 10

In addition to the methods listed in Examples 6–9, sodium methyl N-cyanodithioiminocarbonate can be prepared in solvents such as aqueous ethanol (5 to 75% water, preferably 50% water) and at temperatures between 0° and 50° C. Furthermore, other methylating agents, such as dimethyl sulfate or methyl chloride, could be used in place of methyl iodide.

Potassium Methyl N-Cyanodithioiminocarbonate

EXAMPLE 11

Dipotassium N-cyanodithioiminocarbonate (348.2 g, 1.794 mol, 1.0 equiv), water (1.575 L), and acetone (1.450 L) were charged into a 5-L, three-necked, round-bottomed flask equipped with a mechanical stirrer, thermometer, a fritted glass inlet tube and an exit tube. The solution was cooled to 3° C. and methyl chloride (102.8 g, 2.036 mol, 1.13 equiv) was added over 70 minutes while the temperature was maintained at less than 7° C. The reaction mixture was stirred overnight and then concentrated to give a wet yellow-white paste which was suspended in acetone (1.25 L; 4 mL/g of product) and stirred for 5 minutes. The mixture was filtered to yield 124 g (93%) of white potassium chloride. A sample of this solid was dissolved in water to give a clear colorless solution indicating that all the starting dipotassium salt had been consumed. The filtrate was concentrated in vacuo at 50° C. to a yellow-white solid, which was suspended in methylene chloride (900 mL; 3 mL/g of product; to remove dimethyl N-cyanodithioiminocarbonate side product) and was stirred for about 30 minutes. The solid was collected by filtration, washed with methylene chloride (100 mL) and dried to yield 235 g (77%) of a white, crystalline solid (mp: 212°–217° C.). The 1H NMR was consistent with the structure. The methylene chloride filtrate was washed with water (100 mL), dried (MgSO$_4$), filtered and concentrated to yield 7.6 g (5.8%) of dimethyl N-cyanodithioiminocarbonate.

EXAMPLE 12

Cyanamide (15.1 g of a 50% aqueous solution, 180 mmol, 1.0 equiv), 95% ethanol (36 mL), and carbon disulfide (13.7 g, 180 mmol, 1.0 equiv) were charged into a 250-mL, three-necked round-bottomed flask equipped with a stirring bar, thermometer, and addition funnel. Potassium hydroxide (23.74 g, 360 mmol, 2.0 equiv, in 120 mL of 20% aqueous ethanol) was charged to the addition funnel and was added over 38 minutes while the reaction temperature was maintained at about 8° C. The mixture was stirred for 2.5 h and to the resulting slurry was added methyl chloride (12.6 g, 249 mmol, 1.38 equiv) over 1 h while the temperature rose to 45° C. The reaction mixture was stirred 1 h and was concentrated to a yellow-white paste. Acetone (125 mL; 4mL/g of product) was added to the paste and the mixture was stirred for 30 minutes. The mixture was filtered to yield 16.2 g of wet, white potassium chloride. A sample of this solid was dissolved in water to give a clear, colorless solution indicating that all the starting dipotassium salt had been consumed. The filtrate was concentrated at 50° C. to a yellow-white solid, which was suspended in methylene chloride (200 mL; 3 mL/g of product; to remove dimethyl N-cyanodithioiminocarbonate side product) and was stirred for about 30 minutes. The solid was collected by filtration, washed with methylene chloride (10 mL) and dried to yield 26.0 g (85%) of a faint pink crystalline solid which is potassium methyl N-cyanodithioiminocarbonate. The methylene chloride filtrate was concentrated to yield 1.7 g (9%) of dimethyl N-cyanodithioiminocarbonate.

EXAMPLE 13

Cyanamide (125.4 g of a 50% aqueous solution, 1.491 mol, 1.0 equiv), 95% ethanol (350 mL), and carbon disulfide (120 g, 1.576 mol, 1.05 equiv) were charged into a 1-L stainless steel autoclave. The system was sealed and potassium hydroxide (14.0M, 214.8 mL, 3.007 mol, 2.0 equiv) was pumped in over 20 minutes while the reaction temperature was maintained at under 30° C. Water (30 mL) was used as a rinse for the injection tube to insure that all the hydroxide had reached the reaction mixture. The mixture was stirred for 3 h and then methyl chloride (91.7 g, 1.82 mol, 1.21 equiv) was added over 1.75 h while a reaction temperature of 40° C. was maintained. After 45 minutes, the reaction mixture was concentrated to ⅔ volume and was divided into three 220 mL portions. Portion A was concentrated to a yellow-white paste which was suspended in acetone (340 mL; at 4 mL/g of product), stirred for 30 minutes and filtered. Wet potassium chloride was obtained (about 40 g) and the filtrate was concentrated to yield 75.3 g (88.6%) of potassium methyl N-cyanodithioiminocarbonate after drying for 2 h in a vacuum oven. Portion B was stored overnight and concentrated to a yellow-white paste. The water was chased with 95% ethanol (50 mL), and the paste was suspended in acetone (320 mL) and stirred for 0.5 h. The mixture was filtered to yield wet potassium chloride and the yellow filtrate was dried (Na2SO$_4$), filtered and concentrated. The yield of dry product was 73.3 g (86%) as a granular yellow solid. This treatment of the product indicated that there was little decomposition of the potassium methyl adduct upon storage in the reaction mixture for about 12 hours. Portion C was treated with hydrazine as described in Example 18.

EXAMPLE 14

Cyanamide (125.4 g of a 50% aqueous solution, 1.491 mol, 1.0 equiv), methanol (350 mL), and carbon disulfide (127.6 g, 1.676 mol, 1.12 equiv) were charged into a 1-L stainless steel autoclave. The system was sealed and potassium hydroxide (14.0M, 210 mL, 2.982 mol, 2.0 equiv) was pumped in over 20 minutes while the reaction temperature was maintained at under 25° C. Water (30 mL) was used as a rinse for the injection tube to insure that all the hydroxide had reached the reaction mixture. The mixture was stirred for 2 h and analysis of the reaction mixture indicated complete consumption of the cyanamide had occurred and that the pH was 7.5. Methyl chloride (75 g, 1.485 mol, 1.04 equiv) was added over 15 minutes while a reaction temperature of 35° C. was maintained. After 1.25 h, the reaction mixture was concentrated to a yellow-white paste. The water was chased with 95% ethanol (100 mL) and the paste was suspended in methanol (500 mL) and stirred for 0.5 h. The mixture was filtered to yield potassium chloride (dried by vacuum, 105 g, 95%), the filter case was washed with methanol (2×100 mL), and the yellow filtrate was concentrated. The resulting yellow paste was washed with methylene chloride (750 mL) and filtered.

Analysis (TLC) of the potassium chloride solid and methylene chloride filtrate indicated that product was present in both. Thus, methanol cannot be used to separate the product from potassium chloride for purification.

The potassium chloride was washed with acetone (100 mL) and filtered. The methylene chloride filtrate was concentrated and the yellow-white paste was dissolved in acetone (375 mL) and filtered to remove a small amount of potassium chloride.

The acetone layers were combined and concentrated and the yellow-white paste was suspended in methylene chloride (300 mL) for 0.5 h. The mixture was filtered and the filter cake was washed with methylene chloride (100 mL) to yield 106 g KCl (95%) and 232 g (91%) of the desired potassium methyl product as a yellow-white powder (mp: 207° C.). The product was identified by $^1$H and $^{13}$C NMR spectra.

3-Mercapto-5-amino-(1H)-1,2,4-triazole

The desired product 3-mercapto-5-amino-(1H)-1,2,4-triazole can be prepared from a mono-S-substituted N-cyanodithioiminocarbonate such as sodium methyl N-cyanodithioiminocarbonate or potassium methyl N-cyanodithioiminocarbonate prepared according to any of the methods listed in Examples 6 through 14 above.

EXAMPLE 15

A solution of potassium methyl N-cyanodithioiminocarbonate (170 g, 1.0 mol; Portions A and B of Example 13) in water (250 mL; 40 weight %) was filtered by gravity to remove insoluble solids and warmed to 45° C. Hydrazine hydrate (54.4% in water, 32.09 g, 1.0 mol) was added dropwise over 20 min while maintaining the temperature at less than 60° C. The methane thiol produced was removed from the reaction vessel with a stream of nitrogen. The reaction mixture was stirred at about 50° C. for 1.2 h and then the mixture was allowed to cool to room temperature overnight. The solution was filtered to remove any insoluble material and was cooled in ice. Concentrated HCl was added (about 65 mL) until pH 6 was reached. The white solid was collected by filtration, washed with water (200 mL) and dried to yield 92 g (79%) of the desired 3-mercapto-5-amino-(1H)-1,2,4-triazole (purity: 96.7% (HPLC)).

EXAMPLE 16

A solution of potassium methyl N-cyanodithioiminocarbonate was prepared according to Example 13, using 1.25 moles of cyanamide, and approximately the same reaction times and temperatures. The reaction mixture containing the mono-methyl adduct was concentrated at 50° C. at aspirator vacuum to remove the ethanol. The residue was diluted with water (300 mL) to give an aqueous solution of potassium methyl N-cyanodithioiminocarbonate of 25 wt %. The solution was treated with hydrazine hydrate (about 74 g of a 54.4 wt % aqueous solution, 1.255 mol, 1.0 equiv) in the same manner as given in Example 15, except that the addition required 45 minutes. The 3-mercapto-5-amino-(1H)-1,2,4-triazole product was precipitated by acidification of the reaction mixture to pH 5 and was isolated by filtration. The yield of 3-mercapto-5-amino-(1H)-1,2,4-triazole was 96 g (66%) with a purity of 96.5%.

EXAMPLE 17

The experiment of Example 16 was repeated except that 1.496 moles of cyanamide were used and the percentage concentration of potassium methyl N-cyanodithioiminocarbonate after removal of the ethanol and dilution with water was 30 wt %. The product triazole was obtained in like manner to Example 16 except that the pH of the reaction mixture was adjusted to 6. The yield of triazole was 118 g (68%) with a purity of 97.3%.

EXAMPLE 18

Portion C of Example 13, which was a 25 wt % aqueous solution of potassium methyl N-cyanodithioiminocarbonate after dilution with water, was warmed to 45° C. and hydrazine (54.4 wt % in water, 29.44 g, 0.500 mol, approx. 1 equiv.) was added over 33 minutes, and the resulting solution was stirred at 45° C. for 2.25 hours. The solution was cooled to 25° C. and concentrated HCl was added until a pH of 6 was obtained (about 36 mL of conc. HCl). The mixture was stirred for 1 hour and filtered. The filter cake was washed with water (100 mL) and acetone (100 mL) and dried in vacuo to yield 38 g (65.5%) of the triazole of 96.7% purity.

EXAMPLE 19

A solution of potassium methyl N-cyanodithioiminocarbonate was prepared according to Example 16, using 1.499 moles of cyanamide, and about the same time and temperatures except that the solution of dipotassium N-cyanodithioiminocarbonate was kept overnight. The reaction mixture was concentrated to give a percent concentration of 30 wt % of the mono-methyl adduct in water. This aqueous solution was divided into four portions and each portion was treated with hydrazine hydrate according to the method of Example 15 with the parameters listed in the Table, except that the four solutions of the potassium salt of the triazole were stored overnight.

TABLE

| Portion | Equiv. $H_2NNH_2$ | pH | Amount | Yield | Purity (color) |
|---|---|---|---|---|---|
| 1 | 1.25 | 6 | 31 | 72 | 96.4 |
| 2 | 1.50 | 6 | 30.7 | 71 | 96.6 |
| 3 | 1.75 | 5.8 | 29 | 67 | N/D (off-white) |
| 4 | 2.00 | 4.5 | 32 | 74 | N/D (grey) |

N/D = not determined

These results show that use of more than one equivalent of hydrazine is unnecessary to obtain satisfactory product yield and purity in the method of Example 15.

EXAMPLE 20

Potassium methyl N-cyanodithioiminocarbonate (10.0 g, 58.7 mmol, 1.0 equiv; from Example 14) was dissolved in water 15 mL 40 wt %) and hydrazine hydrate (54.4 wt % in water, 3.5 mL, 1.90 g, 59.4 mmol, 1.01 equiv) was added at 30° C. and the solution was stirred for 1 hour. The solution was then heated to 55° C. and 0.5 mL more of hydrazine (54.5% in water) was added. The solution was held at this temperature for 1 hour and stirred overnight with gradual cooling to room temperature. The solution was acidified to pH 4.6 with concentrated HCl and the solid was collected by suction, washed with water, acetone and dried. The yield of the desired triazole was 5.3 g (77%) with a purity of 98.5%. This Example demonstrates that the purity of the triazole is directly dependent on the purity and the types of washes used to purify the potassium methyl salt.

What is claimed is:

1. A process comprising the step of contacting a Group 1 or 2 metal salt of the anion of formula I,

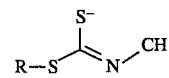

wherein R—S is any suitable leaving group,
with hydrazine or hydrazine hydrate for a sufficient time to form a Group 1 or 2 metal salt of 3-mercapto-5-amino-(1H)-1,2,4-triazole.

2. The process according to claim 1, wherein said metal salt is a potassium or sodium salt.

3. The process according to claim 1, wherein R is selected from substituted or unsubstituted, branched or unbranched $C_1-C_{20}$ alkyl, $C_2-C_{20}$ alkenyl or $C_2-C_{20}$ alkynyl groups;

monocyclic or polycyclic, fused or nonfused, carbocyclic or heterocyclic, substituted or unsubstituted aryl groups;

hydrogen; and non-aryl, monocyclic or polycyclic, fused or nonfused, substituted or unsubstituted heterocyclic groups;

or R—S is selected from thiosulfonates;

sulfonates;

thioesters; and thiocarbamates.

4. The process according to claim 3, wherein R is selected from substituted or unsubstituted, branched or unbranched $C_1-C_6$ alkyl groups.

5. The process according to claim 4, wherein said metal salt of the anion of formula I is sodium methyl N-cyanodithioiminocarbonate.

6. The process according to claim 4, wherein said metal salt of the anion of formula I is potassium methyl N-cyanodithioiminocarbonate.

7. The process according to claim 1, wherein said metal salt of said anion of formula I and said hydrazine or hydrazine hydrate are contacted in a solvent.

8. The process according to claim 7, wherein said solvent is water.

9. The process according to claim 1, wherein said metal salt of said anion of formula I and said hydrazine or hydrazine hydrate are contacted at a temperature ranging from 50° to 60° C.

10. The process according to claim 1, further comprising the step of converting said metal salt of 3-mercapto-5-amino-(1H)-1,2,4-triazole to 3-mercapto-5-amino-(1H)-1,2,4-triazole.

11. The process according to claim 10, wherein said conversion is accomplished by acidification.

12. The process according to claim 11, wherein said acidification is accomplished by adding an amount of acid sufficient to reach a product solution pH ranging from 4 to less than 7.

13. A process comprising the steps of:

(a) contacting cyanamide, carbon disulfide, and a Group 1 or 2 metal hydroxide under conditions sufficient to produce a Group 1 or 2 metal salt of the anion of formula II

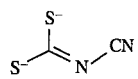

II (b) contacting said Group 1 or 2 metal salt of the anion of formula II of (a) with a compound containing an R-group under conditions sufficient to form a Group 1 or 2 metal salt of the anion of formula I

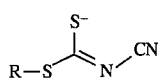

I wherein said R—S group is any suitable leaving group; and (c) contacting the Group 1 or 2 metal salt of the anion of formula I with hydrazine or hydrazine hydrate under sufficient conditions to produce a Group 1 or 2 metal salt of 3-mercapto-5-amino-(1H)-1,2,4-triazole.

14. The process according to claim 13, wherein said metal hydroxide is potassium hydroxide or sodium hydroxide.

15. The process according to claim 14, wherein R is selected from substituted or unsubstituted, branched or unbranched $C_1-C_{20}$ alkyl, $C_2-C_{20}$ alkenyl or $C_2-C_{20}$ alkynyl groups;

monocyclic or polycyclic, fused or nonfused, carbocyclic or heterocyclic, substituted or unsubstituted aryl groups;

hydrogen; and non-aryl, monocyclic or polycyclic, fused or nonfused, substituted or unsubstituted heterocyclic groups;

or R—S is selected from thiosulfonates;

sulfonates;

thioesters; and thiocarbamates.

16. The process according to claim 15, wherein R is selected from substituted or unsubstituted, branched or unbranched $C_1-C_6$ alkyl groups.

17. The process according to claim 16, wherein said metal salt of the anion of formula I is sodium methyl N-cyanodithioiminocarbonate.

18. The process according to claim 16, wherein said metal salt of the anion of formula I is potassium methyl N-cyanodithioiminocarbonate.

19. The process according to claim 14, wherein step (c) is conducted in a solvent.

20. The process according to claim 19, wherein said solvent is water.

21. The process according to claim 14, further comprising the step (d) of converting the sodium salt of 3-mercapto-5-amino-(1H)-1,2,4-triazole to 3-mercapto-5-amino-(1H)-1,2,4-triazole.

22. The process according to claim 14, further comprising the step (d) of converting the potassium salt of 3-mercapto-5-amino-(1H)-1,2,4-triazole to 3-mercapto-5-amino-(1H)-1,2,4-triazole.

23. The process according to claim 14, wherein said compound containing an R-group is methyl chloride, methyl iodide or dimethyl sulfate.

24. The process according to claim 14, wherein step (a) is carried out in a methanolic solvent system.

25. The process according to claim 24, wherein said methanolic solvent system comprises methanol or aqueous methanol.

26. The process according to claim 14, wherein said salt of the anion of formula II produced in step (a) is not isolated prior to step (b).

27. The process according to claim 14, wherein said salt of the anion of formula II produced in step (a) is isolated prior to step (b).

28. The process according to claim 14, further comprising the step of purifying said salt of the anion of formula I with at least one solvent prior to step (c).

29. The process according to claim 28, wherein said purifying renders said salt of the anion of formula I essentially free of contaminants.

30. The process according to claim 28, wherein said solvent is acetone or dichloromethane.

31. The process according to claim 13, wherein step (c) is carried out at a temperature ranging from 50° to 60° C.

32. The process according to claim 13, further comprising the step (d) of converting said Group 1 or 2 metal salt of 3-mercapto-5-amino-(1H)-1,2,4-triazole to 3-mercapto-5-amino-(1H)-1,2,4-triazole.

33. The process according to claim 32, wherein said conversion is accomplished by acidification.

34. The process according to claim 33, wherein said acidification is accomplished by adding an amount of acid sufficient to reach a product solution pH ranging from 4 to less than 7.

35. The process according to claim 13, wherein step (a) is carried out in a methanolic solvent system.

36. The process according to claim 35, wherein said methanolic solvent system comprises methanol or aqueous methanol.

* * * * *

UNITED STATES PATENT AND TRADEMARK OFFICE
CERTIFICATE OF CORRECTION

PATENT NO. : 5,610,311
DATED : March 11, 1997
INVENTOR(S) : Lyndon K. Marble, et al.

It is certified that error appears in the above-indentified patent and that said Letters Patent is hereby corrected as shown below:

Title Page, Item [54] and column 1, in the title, line 3, "N-CYANODITHIOMINOCARBONATE" should read --N-CYANODITHIOIMINOCARBONATE--.

Column 14, line 56, claim 1,

" 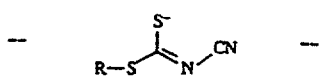 " should read

--  --

Signed and Sealed this

Twentieth Day of May, 1997

Attest:

BRUCE LEHMAN

Attesting Officer

Commissioner of Patents and Trademarks